(12) United States Patent
Wu et al.

(10) Patent No.: US 8,430,111 B2
(45) Date of Patent: Apr. 30, 2013

(54) EFFICIENT LIQUID PROCESSING SYSTEM

(75) Inventors: Rei-Young Amos Wu, Palatine, IL (US); Ashok Shashikant Dhruv, Englewood, CO (US); Paul Konopacki, Arlington Heights, IL (US); Michael J. Mastio, Crystal Lake, IL (US); Richard Schutzenhofer, Naperville, IL (US)

(73) Assignee: Stokely-Van Camp, Inc., Chicago, IL (US)

( * ) Notice: Subject to any disclaimer, the term of this patent is extended or adjusted under 35 U.S.C. 154(b) by 197 days.

(21) Appl. No.: 12/970,154

(22) Filed: Dec. 16, 2010

(65) Prior Publication Data

US 2011/0083752 A1 Apr. 14, 2011

Related U.S. Application Data

(63) Continuation of application No. 11/772,685, filed on Jul. 2, 2007, now Pat. No. 7,874,306.

(60) Provisional application No. 60/817,908, filed on Jun. 30, 2006.

(51) Int. Cl.
*B08B 3/04* (2006.01)
*B08B 9/027* (2006.01)
*A61L 2/18* (2006.01)

(52) U.S. Cl.
USPC ............ 137/15.04; 137/240; 134/22.11; 134/166 C

(58) Field of Classification Search ............ 137/240, 137/238, 15.04, 15.05, 15.01; 134/166 C, 134/22.11
See application file for complete search history.

(56) References Cited

U.S. PATENT DOCUMENTS

| | | | |
|---|---|---|---|
| 4,196,752 A | 4/1980 | Niskanen | |
| 4,917,136 A | 4/1990 | Ohmi | |
| 6,345,642 B1 | 2/2002 | Yoshidome | |
| 7,293,675 B1 * | 11/2007 | Luhn | ............ 137/238 |

OTHER PUBLICATIONS

Office Action dated Mar. 29, 2010 for U.S. Appl. No. 11/772,685, 8 pages.
Notice of Allowance dated Sep. 21, 2010 for U.S Appl. No. 11/772,685, 6 pages.

* cited by examiner

*Primary Examiner* — Kevin Lee
(74) *Attorney, Agent, or Firm* — Banner & Witcoff, Ltd.

(57) ABSTRACT

A fluid processing system has a plurality of segments configured to receive flow of a fluid product. Each of the plurality of segments has a line input, a line output, a cleaning input valve, and a cleaning discharge valve. The cleaning input valve connects to the line input and the cleaning discharge valve connects to the line output. A cleaning medium is provided wherein the cleaning medium is injected into a respective cleaning input valve and drained through a respective cleaning discharge valve, such that each segment can be cleaned independently of each other.

22 Claims, 3 Drawing Sheets

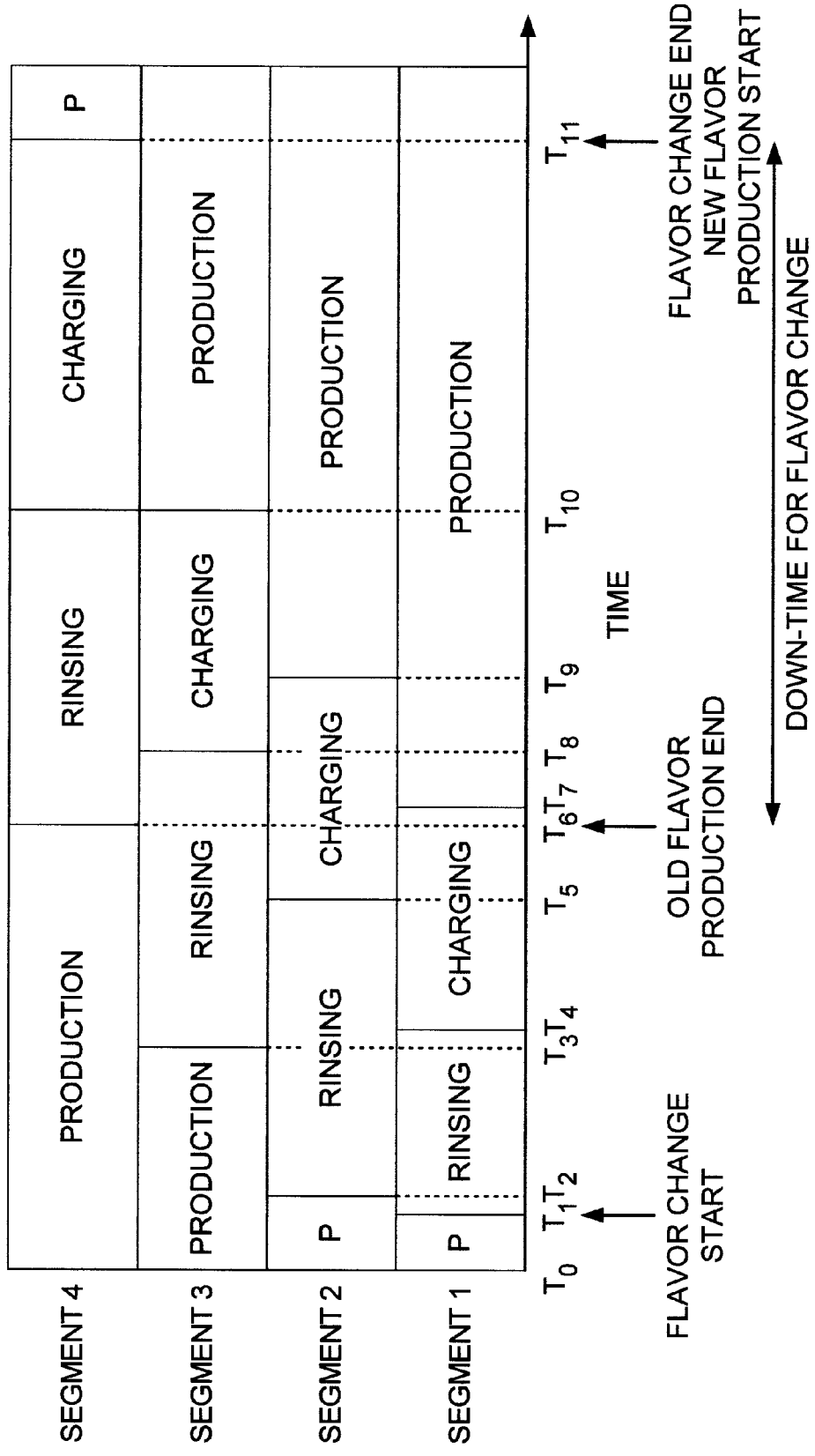

EFFICIENT LIQUID PROCESSING SYSTEM

CROSS REFERENCE TO RELATED APPLICATIONS

This Application is a continuation of prior U.S. application Ser. No. 11/772,685, filed Jul. 2, 2007, now U.S. Pat. No. 7,874,306, which claims the benefit of U.S. Provisional Patent Application No. 60/817,908, filed Jun. 30, 2006, the contents of both U.S. application Ser. No. 11/772,685 and U.S. Provisional Patent Application No. 60/817,908 are fully incorporated herein by reference in their entirety.

FIELD OF THE INVENTION

The present invention relates generally to processing systems for liquid products and more particularly to efficient change-over in a processing system for liquid products.

BACKGROUND OF THE INVENTION

Liquid products, such as beverages, may be batch processed and dispensed into containers. Various types of containers can be used, including cans, cartons, or bottles. Typically, the beverage is pumped through lines and then dispensed into individual containers. Depending on the type of beverage, additional processing may be performed before, during, or after filling. For example, heat or sterilization treatment may be performed on dairy-based beverages.

To provide variety, beverages are offered in different flavors. In conventional production lines, one flavor is produced at a time. The lines need to be cleaned prior to producing a different flavored beverage. Cleaning involves flushing the lines with hot rinse water. Additionally, the production line then needs to be charged with the new liquid product to remove the rinse water. This requires the production line to be completely shut down until cleaning and charging is completed, resulting in significant down-time (e.g., 20-30 minutes) of the production line, as well as high water consumption and product waste.

Thus, from the foregoing discussion, it is desirable to provide an efficient processing system for liquid products. While liquid processing systems according to the prior art provide a number of advantageous features, they, nevertheless, have certain limitations. The present invention seeks to overcome certain of these limitations and other drawbacks of the prior art, and to provide new features not heretofore available.

SUMMARY OF THE INVENTION

In general, in one aspect, the invention relates to a liquid processing system that includes a plurality of processing segments for processing a liquid product. Each processing segment includes structure such as valves to enable independent cleaning to shorten change-over time from one liquid product to another liquid product.

In general, in another aspect, the invention relates to a liquid processing-system that includes a plurality of processing segments for processing a liquid product. Each processing segment includes valves to enable independent cleaning to shorten change-over time from one liquid product to another liquid product. Each segment is equipped with appropriate monitoring instrumentation to accurately indicate the interface for sequencing control.

In general, in yet another aspect, the invention relates to a procedure that maintains thermal balance and presents no interruption in a sterilization process.

These and other objects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 3 shows a schematic timing diagram of a change-over process in accordance with one embodiment of the invention.

DETAILED DESCRIPTION

The present invention relates to a processing system for producing liquid products efficiently. In one embodiment, the processing system enables the dispensing of different-liquid products efficiently. The liquid products, in one embodiment, comprise consumable liquid products or beverages, such as, for example, fruit juices, sports drinks, tea, milk, or soft drinks. The processing system can be, for example, a hot fill, cold fill, or aseptic fill system. Another type of processing system includes a Carbonated Soft Drink processing system, which is a version of a cold fill processing system. Alternatively, the processing system can be used to fill non-consumable types of liquid products, such as detergents and other cleaners, fabric softeners, paints, and mouthwashes. The processing system can also be used in a Clean-in-Place (CIP) procedure to reduce chemical usages, water, and the time spent to conduct the CIP procedure.

Figure 1:
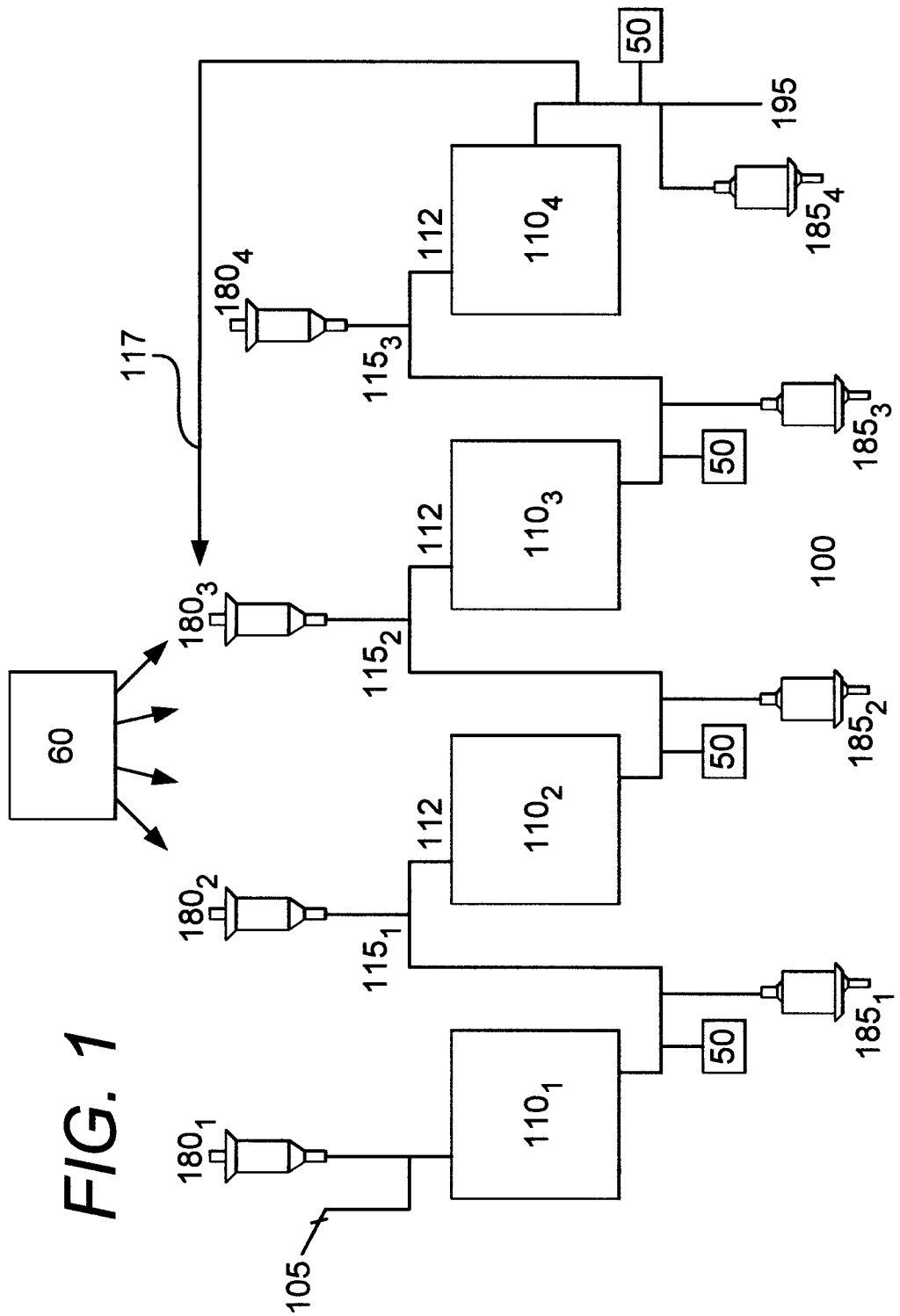
FIG. 1 shows a block diagram of an embodiment of the invention.

FIG. 1 shows a block diagram of a fluid processing system 100 in accordance with one embodiment of the invention. The processing system comprises a production line having a plurality of segments $110_1$ to $110_X$ for processing the liquid product. Ingredients are provided at input 105 and processed by the segments, resulting in finished products at output 195. In addition the fluid processing system 100 includes a recirculation pipe 117, which the operator can use as desired. As shown in one exemplary embodiment, the production line comprises 4 segments $110_1$-$110_4$. (i.e., x=4). Providing a production line having other number of segments is also useful. In one embodiment, x is equal to at least 2.

During production, the liquid product moves from one segment to the next for processing. Once processing is completed at a segment, the liquid product is passed to the next segment for processing. To pass the liquid product from one segment to another, connection pipes $115_{1-X}$ are provided. In one case, the number of connection pipes 115 is equal to x−1 (i.e., x=3). A connection pipe, as shown, is coupled to two segments. For example, one end 111 serves as an output (discharge) end of one segment, while the other end 112 serves as the intake (charge) end for the other segment. As shown, a connection pipe 115 couples two adjacent segments 110. Providing a connection pipe 115 which couples more than two segments 110, or which couples two non-adjacent segments 110 is also contemplated and within the scope of the invention. Additionally, connection pipe 115 serves as a feed back loop from a subsequent segment. In one embodiment, the output end 111 is located at the bottom of a tank that contains the liquid product, while the intake end 112 is located at the top of a tank. Other configurations are also possible and will vary to suit a particular application. Valves may be provided to control the flow of the liquid product from one segment to the next, as well as to suitably isolate segments during production and cleaning processes. It is understood that physical placement of the valves can vary as desired. The valves can be included, for example, in the connection pipes or other components.

Once processing is completed for the batch of liquid product, the production line is prepared for processing a subsequent batch of liquid product. In the case where the subsequent liquid product is different (e.g., different flavor or different type of liquid product), preparation includes flushing the production line to remove the remnants of the previous liquid product and charging it with the subsequent liquid product to be processed.

In one embodiment, the line is sufficiently cleaned and charged to avoid the previous liquid product from negatively affecting the subsequent liquid product. For example, the flavor, texture or characteristics of the subsequent liquid product is not undesirably changed.

Cleaning comprises, for example, flushing the production line with hot water. In accordance with one embodiment of the invention, the segments 110 of the production line can be cleaned independently as opposed to flushing the entire production line from input 105 to output 195 in series fashion. Alternatively, more than one segment 110 can be combined to enable a group or groups of segments 110 to be cleaned independently. For example, a group of segments 110 that includes a feed back connection pipe can be cleaned independently. In one embodiment, the segments, group or groups of segments, or a combination thereof are logically segmented, each capable of being independently cleaned. A segment can refer to a single segment or a group of segments. For example, while segments $110_{1-4}$ can be cleaned independently, a segment group consisting of segments $110_2$ and $110_3$ can be cleaned together as a group by independently of segments $110_1$ and $110_4$.

By providing a production line in which the segments 110 are capable of being independently cleaned, efficiency can be improved. In one embodiment, the cleaning of the segments is staggered, wherein cleaning of a segment commences when processing within that segment is completed. In one embodiment, the cleaning commences after a wait period, measured from the time processing is completed. The length of the wait may depend on the flavor type and the point of the manufacturing process. Commencing cleaning of a segment after completion of processing within the segment effectively reduces the shut-down time of the production line. This is because the shut-down time is then equal to at most the amount of time needed to clean the final processing segment, not the whole production line. The shut down time can further be shortened by commencing the processing of the subsequent liquid product before the cleaning of the final processing segment is completed. In such a case, once the cleaning of the first segment is completed, processing of the next liquid product can begin. It has been found that this arrangement can reduce shut-down time by about 50-75 percent.

In accordance with one embodiment of the invention, a cleaning medium is introduced into the processing segments through cleaning medium input valves $180_{1-x}$ disposed in the connection pipes 115 at generally the intakes 112 of the segments 110. Introducing the cleaning medium at other parts of the processing segments is also useful. In one embodiment, the cleaning medium comprises hot water. Typically, the temperature of the cleaning medium is about 140-180° F. Other types of cleaning medium or temperatures are also possible and will vary to suit a particular embodiment.

To discharge the cleaning medium from the segment, cleaning discharge valves $185_{1-x}$ are provided. In one embodiment, a cleaning discharge valve of a segment is located at the opposite side of the production segment as the cleaning input valve. Discharging the cleaning medium at other locations of the segment is also possible.

It has been found that by injecting the cleaning medium through the connection pipes, mixing of liquid product and cleaning medium is reduced. This is due to the fact that injecting the cleaning medium into the connection pipes produces a sharper transition interface. Less mixing improves cleaning efficiency, reducing time required and amount of cleaning medium needed, as well as the amount of liquid product waste. Reduced product waste results because (1) of a smaller interface and less transition waste, and (2) with accurate sensor and water pushing, almost everything that remains in the pipes and vessels can be packed off.

To further improve cleaning efficiency, automation instruments 50 can be provided in the processing system. The automation instruments 50 can be used to measure, for example, the amount of remnant ingredients of the previous liquid product in the production line. Once the amount remaining reaches an acceptable level, injection of the cleaning medium into-the production line can cease. This can reduce both the amount of cleaning medium and time needed to flush the system. It is understood that a controller 60 can be provided that is operable connected to the segments 110 to control the cleaning and charging of the segments 110.

Figure 2:
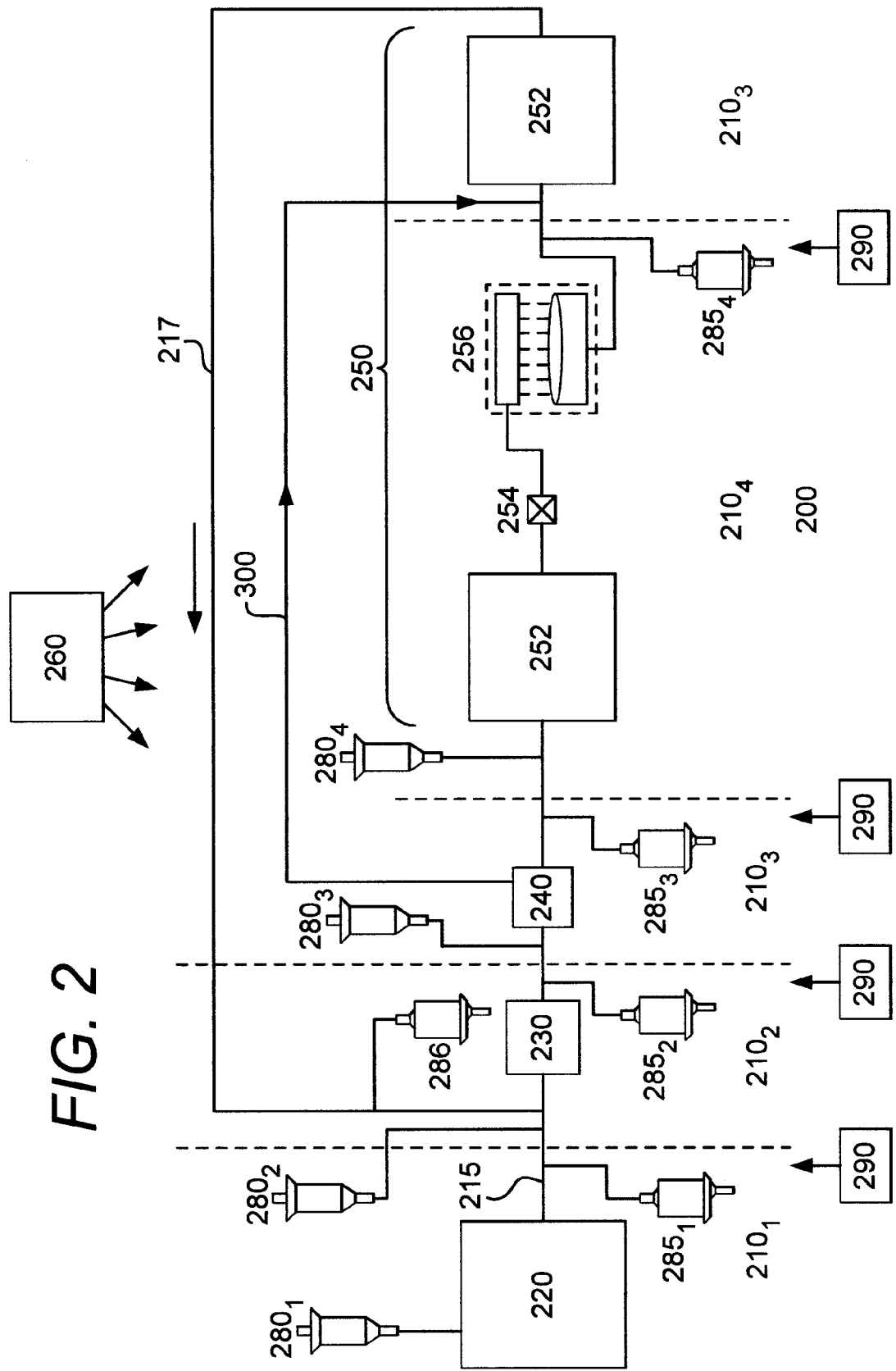
FIG. 2 shows a liquid processing system in accordance with one embodiment of the invention.

FIG. 2 shows a processing system in accordance with one embodiment of the invention. The processing system comprises a hot fill system 200. In a hot fill system, the liquid product is heated to elevated temperatures before it is hot-filled into containers. The heat treatment ensures both the product and container are sterilized, and renders the product shelf-stable.

In one embodiment, the processing system includes a blending tank 220, a balance tank 230, a thermal processing unit 240, and a filler module 250. Flow or connection pipes are provided that couple the blending tank to the balance tank 230, the balance tank 230 to the thermal processing unit 240, and the thermal processing unit 240 to the filler module 250. A return 217 is provided for coupling the filler module 250 to the balance tank 230. Other configurations of the processing system are also possible, such as a continuous blender or a proportional blender to manufacture beverage from concentrates, and a feed to the balance tank.

The liquid product is prepared in the blending tank 220. The balance tank 230 acts as a buffer to compensate for flow rate differences between the blending tank 220 and the thermal processing unit 240. In one embodiment, during processing, the liquid product is continually supplied from the balance tank to the thermal processing unit 240.

The thermal processing unit 240 treats the product with heat to kill micro-organisms, before passing the product to the filler module for hot-filling into containers. The thermal processing unit 240 comprises, for example, a heating station, a holding loop, and/or a cooling station (not shown). Other types of configurations are also possible. In one embodiment, the heating station elevates the liquid product to predetermined temperatures to sterilize the product. The heating station can comprise heaters, including electric heaters, hot water sources and other suitable types of heaters. The product is maintained at the elevated temperature in the holding loop for a time sufficient to kill the microorganisms therein. The product then passes to the cooling station in which it is cooled to a desired temperature.

The heating temperature and holding time required depends on the product. For example, a soft drink beverage may be heated to about 200 to 210° F. for about 25 to 35 sec.

The liquid product is then passed to the filling module 250. In one embodiment, the filling module 250 comprises a filler supply tank 252, a filter 254, a filling station 256 and a filler return tank 258. The liquid product is stored in the filler supply tank 252 and passes to the filling station 256 via the filter 254. The liquid product is hot filled into containers in the filling station 256. The filling station 256 comprises, for example, a multi-head filler. Other types of fillers, such as rotary, linear, volumetric, pressure or gravity fillers, are also possible. After hot fill, the containers are capped or sealed before being transferred to other locations for labeling and packaging. Excess liquid product from the filling station 256 is passed to the filler return tank 258 and then back to the balance tank 230. The line 217 can also be used to direct liquid product to prepare the system.

The hot fill temperature, in one embodiment, should be sufficiently high to effect sterility of both the product and the container surface. The temperature should also be below the softening or melting point of the container. The temperature of the hot filled product is, for example, about 180° F. Other temperatures may also be possible, depending on the application.

In accordance with one embodiment of the invention, the processing system is divided into a plurality of segments. The segments are capable of being independently controlled. In one embodiment, the processing system is divided into four segments $210_{1-4}$. The segments are logically selected in the system to enable efficient change-over. In one embodiment, the first segment includes the product feed pipe 215. The first segment $210_1$ may also include the blending tank 220, if appropriate. For example, when non-dedicated blending tanks are used for processing liquid products, the first segment may include the blending tank as well. The second segment $210_2$ includes the balance tank 230. As for the third segment $210_3$, it includes the thermal processing unit 240 and the filler return tank 258 in the filling module 250 while the forth segment $210_4$ includes the filling module 250 excluding the filler return tank 258. Other segmentations are also possible.

The segments are capable of independent cleaning or preparation. In one embodiment, cleaning is facilitated by locating charge and discharge cleaning valves $280_{1-4}$ at the ends of the segments. For example, a charge cleaning valve $280_1$ is located at one end, while a discharge cleaning valve $285_1$ is located at the other end of a segment. Locating cleaning valves at other points of the segments or providing other configurations of valves is also possible. The filler return tank 258 is considered part of the third segment $210_3$, but is located downstream of the filling station 256. Also an additional discharge cleaning valve 286 may be associated with the filler return tank 258, such as being located off of the return line 217. As further shown in FIG. 2, a filler bypass line 300 is also provided. The filler bypass line 300 allows the fluid product to bypass the filler supply tank 252, the filter 254, and the filling station 256 if desired by an operator. In addition, cleaning medium can be placed into charge cleaning valve $280_3$ and flushed through the thermal processing unit 240, the filler bypass line 300, the filler return tank 258, the return 217, and out through the additional discharge cleaning valve 286 so as to remove the remnant liquid product from the thermal processing unit 240, the filler bypass line 300, the filler return tank 258, and the return 217. This represents an exemplary method to clean the third segment $210_3$. It is appreciated that this can be done independent of the other segments. In a preferred embodiment, the additional discharge cleaning valve 286 is located as close as possible to the product feed pipe 215, such that substantially all excess fluid can be drained out of return 217.

To prepare a segment for change-over, a cleaning medium injected is into a segment 210 via its charge cleaning valve 280. The cleaning medium, in one embodiment, comprises hot water. Other types of cleaning media are also possible such as other fluids, solid materials consisting of particles having abrasive surfaces, or plugs having wiping surfaces. The cleaning medium flushes the old liquid product from the system. A sufficient amount of cleaning medium is injected into the segment to remove the remnant liquid product from the equipment (e.g., pipes, tanks, etc.) of the segment. In one embodiment, the old liquid product is sufficiently removed.

To flush out the cleaning medium, the segment 210 is charged with new liquid product. This can be achieved by, for example, closing the cleaning input valve $280_1$-$280_4$ and charging the segment with new liquid product. The cleaning fluid will discharge through the cleaning discharge valves $285_1$-$285_4$. Once the cleaning medium has been flushed, the cleaning discharge valve is closed.

In one embodiment, the flushing and charging of the segment 210 can be performed with automated instruments, enabling the amount of cleaning medium and new liquid product needed to be determined automatically. For example, meters 290, such as Brix, conductivity meters or mass flow meters, can be used. Other types of meters are also possible. The automated instruments can be used to measure when a sufficient amount of previous liquid product has been removed and when a sufficient amount of new liquid product has been provided to charge the segment. For Sport Beverages, 1400 micro simmons for water/product interface and 200 micro simmons for product/water interface are acceptable threshold amounts or levels. These respective amounts could be in the ranges of 1100-1600 micro simmons and 100-300 micro simmons. The use of automated instruments reduces the cleaning time and amount of cleaning medium consumed and wasted liquid product.

In an alternative embodiment, the segments are prepared using pre-set time periods for cleaning and charging. Other techniques for determining when cleaning and charging is completed are also possible. For example, a combination of automated instruments and preset time periods can be employed.

In one embodiment of the invention, the heating in the thermal processing unit 240 is not interrupted during change-over, keeping the thermal load balanced. By not interrupting the heating during change-over, the need for "come-up" time (i.e., ramping up the thermal unit to the operating temperature) is avoided. This shortens the time needed to prepare the thermal unit 240 for processing the next liquid product. Alternatively, the heating in the thermal processing unit 240 is shut-down during a change-over process to conserve power. In such case, a come-up time is required that extends the time needed to prepare the thermal processing unit for change-over.

As described, the processing system in accordance with the invention is divided into a plurality of independently-controlled segments. During a change-over process, the rinsing and charging steps for each segment can be controlled independently. This allows the rinsing and charging of each segment to be synchronized to enable optimal time overlapping, giving rise to several significant advantages such as shorter down-time and reduced product wastage and water consumption. For example, it has been found that change-over time can be shortened from about 20-30 min to about 7-10 min. Additionally, product waste is reduced by about 40-60%, while water consumption is lowed by about 10-20%.

Each segment, in one embodiment, includes at least one inlet and at least one outlet and a control device for controlling the flow of the liquid products and cleaning medium through the segments. The control devices include, for example, valves controlled by an operating device, such as computerized 2-way valves, 3-way valves, 4-way valves and/or other control devices are also possible. The control device may be operable coupled to an overall controller for the system. Providing separate inlets and outlets for each segment allows the cleaning medium to be supplied to and purged from each segment independently. The inlets and outlets are coupled to, for example, the rinse water supply and return, respectively. The rinse water may be supplied from, for example, a (CIP) circuit or a hot water tank.

In one embodiment, the inlets and outlets are located along pipes. By introducing different types of liquids inside the pipes rather than at the bottom of tanks, mixing of liquids is minimized and the size of the mixing zone between the old liquid product and cleaning medium is reduced. As such, product waste and cleaning medium usage can be reduced. Furthermore, the processing time for each rinsing or charging step can be shortened.

In one embodiment, rinse water supply to and from each segment are regulated by electrically operated valves. In one embodiment, the valves are controlled by a control device including for example, a microcontroller or microprocessor executing a control program, the microcontroller being operably connected to the segments 210 and associated valves $280_1$-$280_4$ and $285_1$-$285_4$ as well as controller 260. The duration of the rinsing steps in each segment may be determined according to pre-programmed timing. The program may be configured, for example, to execute the rinsing steps in each segment in a cascade mode. Different programs, tailored to different combinations of old and new liquid products, may be provided. The microprocessor can also be incorporated with a human machine interface screen to provide the operator with real time visual updates of the operation of the system. Any intervention measures to correct a malfunctioning situation, therefore, can be readily executed.

In another embodiment, a process control system is integrated with the control device to control the valves using real-time process data. The process control system includes automated instruments 290 to monitor the operation of the liquid processing system, ensuring product consistency and reducing process time. For example, Brix meters, conductivity meters, or mass flow meters may be placed at suitable locations to provide timely indication of the product-water transition interface in the pipes. Based on this information, the time for cleaning or charging the segments can be optimized.

In one embodiment of the invention, the process control system includes a set of Brix meters 290 coupled to a microprocessor or overall controller 260. Other automated instruments, for example, flow meters in pipes and/or level detectors in tanks can also be provided. The meters are located, for example, in the connection pipes coupling the segments. The valves regulating rinse water supply to or return from each segment, and the flow of product between segments, are also coupled to the microprocessor. The microprocessor controls the operation of the valves in response to signals from the Brix meters. Each segment includes its respective set of meters for independent operation.

In operation, a Brix meter detects the presence of the old liquid product in the line from its high sugar levels. To prepare for a change-over, rinse water is introduced to a segment via the cleaning charge valve and out through the cleaning discharge valve. The mixing of product and rinse water in the pipe gives rise to a mixing zone. The length of the mixing zone is determined by the degree of flow turbulence in the pipe. The Brix meter detects the mixing zone from the gradual fall in sugar levels. When sugar is no longer detected, signifying that no traces of the old flavor product remains in the pipe, the Brix meter, notifies the microprocessor to close the cleaning charge valve to cut off supply of rinse water.

An appropriate valve is then opened to begin charging the segment with a subsequent liquid product. At the start of the charging step, the subsequent liquid product is introduced to a segment. The subsequent liquid product purges rinse water from the segment/pipe. The mixing zone, which develops as described above, is detected by the Brix meter as a gradual increase in sugar levels. When the concentration of sugar has reached a threshold level, indicating that rinse water has been completely purged from the line, the Brix meter sends a signal to the microprocessor to indicate that charging is complete. The segment is ready for processing the subsequent liquid product. As discussed, it is understood that appropriate valving is provided in the segments to isolate, clean and charge as required.

In an alternative embodiment, conductivity meters may be used in place of Brix meters. In such cases, the different classes of liquids, such as old flavor product, rinse water, and subsequent flavor product are identified by their electrical conductivity. The electrical conductivity of rinse water and new flavor product will serve as thresholds to indicate the end of the cleaning and charging steps, respectively.

FIG. 3 shows the timing of a processing system in operation in accordance with one embodiment of the invention. At time T0, the processing system is producing the old liquid product, which is charged in all the segments. The flavor change process commences at time T1 with a cleaning step in segment 1. At T2 and T3, the cleaning step is started in segments 2 and 3, respectively. While Segments 1-3 are cleaned and charged, the old flavor product is continually hot filled into containers in segment 4. At T6, old liquid production stops and the cleaning step commences in Segment 4. The cleaning step is followed by a charging step in which new liquid product is charged to the system from the blending tank 220. The new liquid product may be prepared in the same blending tank as the old liquid product, or supplied from a different blending tank.

In one embodiment, the charging step in segments 1-4 commences at T4, T5, T8 and T10, respectively, and ends at T7, T9 and T10, in segments 1-3, respectively. At the end of the charging step, the respective segment is charged with the new flavor product and ready for production. The flavor change process is complete and production of the new flavor product commences when the charging step in Segment 4 ends at T11.

It should be understood that the present invention is not limited to the timing described herewith. The cleaning and charging steps may be of different durations in each segment depending on the holding capacity of the segment and rinse water flow rate therethrough. The time lag, T1-T2, T2-T3, and T3-T6, between start of rinsing in adjacent segments can be adjusted as desired to optimize the flavor change process. Other factors that may be considered for optimization include the speed of the filler, the level of the tanks, the pump speed, the rinsing water temperature, and/or the type of flavor transfer out of and transfer into.

Accordingly, down-time for product change can potentially be shortened by reducing the lag time between cleaning steps in adjacent segments, and that between charging steps in each segment. For example, production in segment 4 is continued simultaneously with charging of segments 1 and 2, and rinsing of segment 3. Subsequently, by the time cleaning is completed in segment 4, the upstream segments 1-3 are completely charged and ready for production. Therefore, the effective down-time during which there is no production is only from T6 to T11.

The invention may be embodied in other specific forms without departing form the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A fluid processing system comprising:
a first segment and a second segment both configured to receive flow of a fluid product, the first segment and the second segments having a line input, a line output, a cleaning input valve, and a cleaning discharge valve, wherein the cleaning input valve connects to the line input and the cleaning discharge valve connects to the line output, wherein the line output of the first segment is connected to the line input of the second segment to provide for fluid from the line output of the first segment to the line input of the second segment; and
wherein the cleaning input valves are configured to receive a cleaning medium and the cleaning discharge valves are configured to drain the cleaning medium, such that the first segment and the second segment can be cleaned independently of each other.

2. The fluid processing system of claim 1 wherein the segments form one of a hot fill system, a cold fill system, and an aseptic system.

3. The fluid processing system of claim 2 further comprising a third segment and a fourth segment.

4. The fluid processing system of claim 3 wherein the line output of the first segment is the line input for the second segment, the line output for the second segment is the line input for the third segment, and the line output for the third segment is the line input for the fourth segment.

5. The fluid processing system of claim 3 wherein more than one segment can be grouped together such that the group can be cleaned independently of the other non-grouped segments.

6. The fluid processing system of claim 1 further comprising a control device operably connected to the segments that determines and controls the amounts of fluid product and cleaning medium in each segment.

7. The fluid processing system of claim 4 wherein the segments are capable of being isolated from one another wherein once the liquid product is passed from the first segment to the second segment, the first segment is cleaned with the cleaning medium.

8. The fluid processing system of claim 4 wherein when the fourth segment is being cleaned with the cleaning medium, the first, second and third segments are placed in a position to be charged with a second amount of fluid product.

9. A method of operating a filling process comprising the steps of:
transferring a fluid product to a first segment;
transferring the fluid product to a second segment from the first segment;
transferring the fluid product to a third segment from the second segment;
transferring the fluid product to a fourth segment from the third segment; and
cleaning the first segment, second segment, third segment, or the forth segment while the fluid product is in an adjacent segment.

10. The method of claim 9 wherein the step of cleaning the first, second, third and fourth segments consists of injecting a cleaning medium into a cleaning input valve and flushing the cleaning medium out of a cleaning discharge valve.

11. The method of claim 10 where in the step of flushing the cleaning medium, the segment is charged with a new amount of liquid product such that the cleaning medium is flushed through the cleaning discharge valve.

12. The method of claim 11 wherein the step of injecting the cleaning medium is controlled by at least one metering device which measures the amount of cleaning medium and determines the amount of cleaning medium that is placed into the segment and the step of flushing the cleaning medium is controlled by the at least one metering device which measures the amount of new fluid product and determines the amount of new fluid product that is placed into the segment.

13. The method of claim 12 wherein the at least one metering device is at least one of a Brix meter, a conductivity meter, and a flow meter.

14. The method of claim 9 wherein the first segment includes a blending tank, the second segment includes a balance tank, the third segment is a thermal processing unit, and the fourth segment is a filling module.

15. The method of claim 9 where in the steps of cleaning the first, second, third, and fourth segments more than one segment can be grouped together such that the group can be cleaned independently of the other non-grouped segments.

16. The method of claim 9 wherein the cleaning medium is heated to about 140-180° F. before inserting the cleaning medium into the cleaning input valve.

17. A method of cleaning a fluid processing system comprising the steps of:
providing a plurality of segments, each segment having a line input and a line output; wherein a line output of one of the plurality of segments is a line input of another segment;
providing the line input with a cleaning input valve;
providing the line output with a cleaning discharge valve;
inserting a cleaning medium into the cleaning input valve;
cleaning the system with the cleaning medium;
flushing the cleaning medium through the cleaning discharge valve; and
closing the discharge valve.

18. The method of claim 17 wherein the cleaning medium is heated to about 140-180° F. before inserting the cleaning medium into the cleaning input valve.

19. The method of claim 17 wherein the line input is charged with new fluid product so as to cause the cleaning medium to discharge through the cleaning discharge valve.

20. The method of claim 19 further comprising the step of metering the amounts of new fluid product and cleaning medium with a metering device so as to determine the amounts needed to clean and charge the segment.

21. The method of claim 20 wherein the metering device is at least one of a Brix meter, a conductivity meter, and a flow meter.

22. The method of claim 17 wherein the cleaning medium is injected into a respective cleaning input valve and drained through a respective cleaning discharge valve, such that each segment can be cleaned independently of each other.

* * * * *